US012580069B2

(12) United States Patent
Glatz et al.

(10) Patent No.: US 12,580,069 B2
(45) Date of Patent: Mar. 17, 2026

(54) AUTOMATIC SETTING OF IMAGING PARAMETERS

(71) Applicant: Brainlab AG, Munich (DE)

(72) Inventors: Florian Glatz, Kaufering (DE); Sebastian Stopp, Munich (DE)

(73) Assignee: Brainlab SE, Munich (DE)

( * ) Notice: Subject to any disclaimer, the term of this patent is extended or adjusted under 35 U.S.C. 154(b) by 308 days.

(21) Appl. No.: 17/279,915

(22) PCT Filed: Feb. 14, 2020

(86) PCT No.: PCT/EP2020/053990
§ 371 (c)(1),
(2) Date: Mar. 25, 2021

(87) PCT Pub. No.: WO2020/165449
PCT Pub. Date: Aug. 20, 2020

(65) Prior Publication Data
US 2021/0343396 A1 Nov. 4, 2021

(30) Foreign Application Priority Data
Feb. 14, 2019 (WO) ................ PCT/EP2019/053698

(51) Int. Cl.
*G16H 30/20* (2018.01)
*A61B 6/00* (2024.01)
(Continued)

(52) U.S. Cl.
CPC .......... *G16H 30/20* (2018.01); *A61B 6/5258* (2013.01); *A61B 6/547* (2013.01); *G16H 10/60* (2018.01); *G16H 40/40* (2018.01); *G16H 40/63* (2018.01)

(58) Field of Classification Search
USPC ....................................................... 705/2–3
See application file for complete search history.

(56) References Cited

U.S. PATENT DOCUMENTS

2010/0174180 A1* 7/2010 Rousso .................. G16H 30/40
600/431
2017/0000447 A1* 1/2017 Profio .................... A61B 6/461
(Continued)

FOREIGN PATENT DOCUMENTS

EP 1946702 A1 7/2008
EP 3054390 A1 8/2016
(Continued)

OTHER PUBLICATIONS

Panse, A. (2012). Improved region of interest imaging (Order No. 3541144). Available from ProQuest Dissertations and Theses Professional. (1114042574). Retrieved from https://dialog.proquest.com/professional/docview/1114042574?accountid=131444 (Year: 2012).*
(Continued)

*Primary Examiner* — Bennett Stephen Erickson
(74) *Attorney, Agent, or Firm* — Tucker Ellis LLP

(57) ABSTRACT
The present application relates to a computer-implemented medical method of determining a patient-specific setting of at least one imaging parameter of an imaging device. The method includes acquiring patient data describing information relating to a patient and having impact on the setting of at least one imaging parameter of the imaging device and acquiring object data describing at least one property of at least one object of interest associated with the anatomy of the patient. The imaging parameter data is determined based on the patient data, describing a patient-specific setting of the at least one imaging parameter of the imaging device.

15 Claims, 3 Drawing Sheets

(51) Int. Cl.
    *G16H 10/60*    (2018.01)
    *G16H 40/40*    (2018.01)
    *G16H 40/63*    (2018.01)

(56)                    References Cited

U.S. PATENT DOCUMENTS

| | | | | |
|---|---|---|---|---|
| 2017/0154231 A1* | 6/2017 | Keil | ..................... | A61B 5/0033 |
| 2018/0021097 A1* | 1/2018 | Quaid | .................... | A61B 34/10 |
| | | | | 600/407 |
| 2018/0129896 A1 | 5/2018 | Wu et al. | | |
| 2020/0218922 A1* | 7/2020 | Chen | ...................... | A61B 6/469 |
| 2020/0268339 A1* | 8/2020 | Hao | ....................... | A61B 6/544 |
| 2021/0386389 A1* | 12/2021 | Freiman | ................. | A61B 6/541 |
| 2021/0391078 A1* | 12/2021 | Kim | ......................... | G06N 3/08 |

FOREIGN PATENT DOCUMENTS

| | | | |
|---|---|---|---|
| WO | 2009075714 A1 | 6/2009 | |
| WO | 2018153473 A1 | 8/2018 | |

OTHER PUBLICATIONS

International Search Report and Written Opinion for corresponding international application No. PCT/EP2020/053990, dated Apr. 3, 2020. 10 pages.

* cited by examiner

S11: acquiring patient data

S12: acquiring object data

S13: determining parameter data

<u>Fig. 2</u>

AUTOMATIC SETTING OF IMAGING PARAMETERS

RELATED APPLICATION DATA

This application is a national phase application of International Application No. PCT/EP2020/053990, filed Feb. 14, 2020, which claims priority to International Application No. PCT/EP2019/053698, filed on Feb. 14, 2019, the contents of both of which are incorporated herein by reference.

FIELD OF THE INVENTION

The present invention relates to a computer-implemented method for automatically setting at least one imaging parameter of an imaging device, a corresponding computer program, a program storage medium storing such a program and a computer for executing the program, as well as a medical system comprising an electronic data storage device and the aforementioned computer.

TECHNICAL BACKGROUND

Prior to diagnostic, therapeutic or surgical medical procedures to be performed on a patient, a visual representation of the patient's anatomy is regularly obtained by creating a two-dimensional or even a three-dimensional image(-dataset) of relevant regions of the patient's anatomy. The most commonly used imaging modalities for obtaining such images or image-datasets in a medical field are radiography, magnetic resonance imaging (MRI) and tomography including X-ray computed tomography (CT). Since the corresponding imaging devices have to deliver usable images for a large range of different anatomical structures and for a large range of different circumstances, such imaging devices have to allow for an adjustment of the imaging parameters that define the characteristics the imaging device is working with. Such imaging parameters can for example define at which spatial position (spatial location and/or spatial orientation) the imaging device is positioned with respect to the anatomical structure of interest for obtaining a desired image, or how structures of certain physical properties are displayed in a later image.

Thus, the imaging parameters of such imaging devices have to be readjusted each time the underlying circumstances or the desired outcome of the imaging procedure change.

This problem is most commonly encountered by acquiring one or more "test images" to check whether the currently set imaging parameters of the imaging device deliver a desired outcome, i.e. a usable image(-dataset). This approach, however, not only comes with a rather lengthy and therefore expensive preparation of the actual imaging procedure, but, more seriously in some imaging modalities, with an increased dose of radiation applied to the patient.

It is the object of the present invention to provide a fast and easy approach to set at least one imaging parameter of an imaging device, that the imaging device delivers a desired outcome or usable image(-dataset), respectively.

The present invention can be used for any kind of imaging procedures e.g. in connection with a system adapted to acquire MR-images, CT-images or CBCT images.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION OF THE INVENTION

In the following, a short description of the specific features of the present invention is given which shall not be understood to limit the invention only to the features or a combination of the features described in this section.

The invention relates to an approach for determining a patient-specific setting or value for at least one imaging parameter of an imaging acquiring device on the basis of data describing the patient the medical image is to be taken of, and on the basis of data describing at least one property of at least one object of interest associated with the anatomy of the patient, both of which has or is at least expected to have influence on the outcome of the imaging procedure. In this context, the patient-related data describes properties of the patient's anatomy and/or of a medical procedure to be performed on the patient, which necessitates a specific setting of at least one imaging parameters of the imaging device. The object data may relate to actual objects that will also be depicted in the at least one image to be acquired, and/or may also relate to virtual objects defined, automatically by a computer or manually by a user, with respect to the patient's anatomy. Further, the object data may be acquired in a DICOM-format. Actual objects and/or virtual objects may be represented by implants, bone screws and the like which are already set or are planned to be set within the patient's body, respectively. At least one imaging parameter of the imaging device can be set to a default, but yet still adjustable value that is expected to deliver a desired outcome of the imaging procedure, i.e. the most meaningful depiction of medical objects and/or anatomical structures within the image to be acquired.

GENERAL DESCRIPTION OF THE INVENTION

In this section, a description of the general features of the present invention is given for example by referring to possible embodiments of the invention.

In general, the invention reaches the aforementioned object by providing, in a first aspect, a computer-implemented medical method of determining a patient-specific setting of at least one imaging parameter of an imaging device. The method comprises executing, on at least one processor of at least one computer (for example at least one computer being part of a navigation system), the following exemplary steps which are executed by the at least one processor.

In a (for example) first step of the method in accordance with the present invention, patient data is acquired, which describes information relating to a patient and having impact on the setting of at least one imaging parameters of the imaging device. In other words, information is retrieved which has or at least is expected to have an impact on the outcome of the imaging procedure. This information may relate to the patient as such, particularly the patient's anatomy, but may also relate to a later diagnostic, therapeutic or surgical procedure that will be performed based on the image(-dataset) acquired during the imaging procedure. For example, the patient's body height may have a direct impact on the spatial position the imaging device (this may include a radiation source and a radiation detector) has to be placed at, wherein the patient's disease has of course a direct impact on a planned treatment procedure, which in turn may have influence on the necessary spatial position of the imaging device with respect to the patient. Further, possible implants within the patient's body as well as the patient's weight may have influence on certain imaging modalities or parameters, since implants may cause artifacts in the image, wherein the anatomy of obese patients may necessitate a higher radiation dose to obtain a meaningful detection of inner organs.

All of this data relating to the patient and to a planned procedure may have already been acquired in the past, for example during prior diagnostic, therapeutic or surgical procedures and stored, for example, in a database or on a storage device connected to a medical navigation system. Further, data may also be obtained from a planning procedure that has already been carried out for a future medical procedure.

In addition to the patient data, object data is determined in a (for example) second step. The object data describes at least one property of at least one object of interest associated with the anatomy of the patient. For example, the object data may describe at least one desired spatial position or trajectory for a medical instrument, implant or device with respect to a patient's anatomy, which may also have impact on at least one imaging parameter of the imaging device. For example, it is desirable to acquire images in predefined directions with respect to an instrument trajectory in order to obtain the most usable information as to where the trajectory will be placed with respect to the patient's anatomy. For example, such imaging directing may be, as far as possible, perpendicular or parallel to a desired instrument trajectory. Moreover, an object of interest may relate to a virtual representation of a anatomical structure which may be obtained from an anatomical atlas or from a segmented image of the patient's anatomy, which may then be registered with the patient's actual anatomy. For example, an object of interest may relate to virtual representation of a pathological structure which may be obtained from a segmented image of the patient's anatomy, e.g. using an anatomical atlas, which may then be registered with the patient's actual anatomy. For example, the imaging trajectory of the imaging device may be positioned such that it does not cross sensitive organs that have a low radiation tolerance. Further, the imaging trajectory may be oriented such that specific structures or regions of interest are not superimposed in a later image. Further, an image trajectory may be positioned to extend, as far as possible, perpendicular to an elongated anatomical structure in order to deliver the most usable information about that structure.

All in all, imaging parameters may be set to a specific value in order to get the most usable information out of an image to be acquired. The information about the properties of actual or virtual objects placed with respect to the patient's anatomy helps here. Any property of a virtual object may be defined specifically for a patient, i.e. may have a patient-specific value.

The object data can describe the spatial position, shape, and/or size of one or more implants present in the patient, or of one or more implants to be placed in the patient's anatomy during a later procedure If two or more objects are present, the spatial position of the imaging device can be chosen to optimally image the objects at once, e.g. by keeping them in the field of view without overlap or with a minimum of overlap. For example, the imaging direction can be chosen to be, as far as possible, substantially perpendicular to one or more straight lines connecting the two or more objects. Further, to determine the imaging direction, a three-dimensional model of a plurality of objects to be imaged can be virtually projected in a plurality of directions, e.g. onto a 2D plane, from which a direction is selected as the imaging direction for the imaging-apparatus, which comes along with the least overlap or even with no overlap of the objects. Thus, in a third step of the inventive method, imaging parameter data is determined based on the patient data and the object data, describing a patient specific setting of the at least one imaging parameter of the imaging device.

It is the basic idea of the present invention, to access and utilize the formerly disregarded information for shorten or even superseding formerly necessary preparatory steps of an imaging procedure. For example, the dose level of the imaging device may be set to a higher value when the received patient data shows an above average body weight of the patient. In another example, the radiation source and the radiation detector of an imaging device may be positioned at certain locations and/or orientations with respect to the patient's anatomy, such that a later obtained image shows a certain structure of interest (e.g. organs, implants or pathological structures) at a meaningful angle, or the imaging device may positioned such that certain radiation sensitive structures are not harmed by radiation emitted by the imaging device during imaging acquisition.

In an example of the inventive method, the patient data is acquired from a medical navigation system which is operably coupled to the imaging device. In this regards, a communication protocol may be established, which allows the medical navigation system to communicate with the imaging device, such that the relevant patient data can be transferred from the navigation system to the imaging device. In this context, any conceivable data transmitting means can be used, such as wire-based or wireless communication means, or even storage devices such as hard drives or flash drives, which can be selectively coupled to either one of these devices so as to transfer data between these devices.

In a further example, the step of acquiring patient data involves selecting a dataset of the patient, which in particular includes the patient's name and/or ID. For example, medical personnel may begin the preparation of an imaging procedure by selecting a dataset that stores information about the patient an image(-dataset) is to be acquired from. In case all relevant or necessary information for setting up the imaging device is available, the entire imaging preparation procedure may be carried out fully automatically, such that no preparatory effort is necessary, or the preparatory effort for medical personnel is reduced to selecting the patient dataset, for example by typing in the patient's name or ID, and/or to confirm that the automatically set values for the imaging parameters shall be used for the following imaging procedure. In case some data is missing in the dataset, the affected imaging parameters may be set to a default, non-patient-specific value, which is then manually set by a subsequent user-input. After all necessary imaging parameters of the imaging device have been set, the actual imaging procedure can be initiated.

For example, the information relating to the patient includes, but is of course not limited to, at least one of the following information:

the patient's age;

the patient's gender;

the patient's weight;

the patient's height;

a type of disease of the patient and/or a type of an associated, particularly scheduled treatment procedure;

a position, size and/or shape of a region to be imaged;

a spatial registration of the patient with respect to previously acquired image data.

Further, the at least one imaging parameter on which basis the imaging device may be controlled, can be selected from the following list, which is of course not exhaustive:

a position of the isocenter of the imaging device with respect to the patient's anatomy;

a position, size and/or shape of the imaging region with respect to the patient's anatomy, with respect to objects coupled the patient's anatomy and/or with respect to the imaging device;

a position of a scan trajectory with respect to the patient's anatomy and/or with respect to objects coupled the patient's anatomy;

a position of the imaging device with respect to the patient's anatomy and/or with respect to objects coupled the patient's anatomy;

a position, size and/or shape of a collimator opening of the imaging device;

a scan voltage and/or scan current of an x-ray tube;

a dose modulation;

a selection of a reconstruction kernel and algorithm;

a metal artefact reduction modality;

a subtraction angiography modality;

a dual-energy imaging modality;

a number of x-ray pulses per second;

a number of acquired projections;

a modality and/or setting for post-processing at least one image obtained with the imaging device.

While the above lines outline the general concept of the inventive idea to base imaging parameter settings of an imaging device on data about a patient and/or an upcoming medical procedure, the present invention may in this context include an optimization process so as to find the best possible parameter settings for the imaging device.

The at least one imaging parameter may be set to a specific value for one single 2D-or 3D-image, but such values may also be determined for each image of a plurality of 2D- or 3D-images. For example, imaging parameter values may be determined for a series of images which may be for example taken at predefined intervals, particularly while the imaging device moves with respect to the patient's anatomy, for example along a circular path around the patient. Moreover, the plurality of images may also refer to two or three 2D-images taken along different directions, preferably perpendicular directions, in order to obtain image information for more than two spatial dimensions.

For example, determining imaging parameter data involves determining, based on a first subset of information relating to the patient, a preset of at least one predetermined imaging parameter setting. For example, this first subset may include at least one of the patient's age, the position, size and/or shape of a region to be imaged, the type of disease of the patient and/or the type of an associated treatment procedure. Based on the data of this first subset, the setting of at least some of the imaging parameters may be set to a, particularly preliminary, default value. Upon this preparatory step, the value of at least one further imaging parameter or of at least one already set imaging parameter may be set and/or optimized on the basis of data from a second subset of information relating to the patient, which may include at least one of:

the patient's gender;

the patient's weight;

the patient's height;

a spatial registration of the patient with respect to previously acquired image data.

As has already been indicated further above, the imaging device to be controlled on the basis of patient- and/or procedure-relating data can be any device for obtaining patient images for a medical purpose, including but not limited to an X-ray imaging device, a cone-beam-computedtomography (CBCT) scanner or a computer-tomography (CT) scanner. In order to establish the determined parameter settings relating to a spatial position of the imaging device with respect to the patient, the imaging device may be adapted to be spatially tracked, e.g. by being provided with tracking markers that allow a tracking system to determine the current spatial position of the imaging device with respect to the patient. Based on this information, it is possible to output data to medical personnel or a motorized carrier of the imaging device to reposition the imaging device from its current position to the desired spatial position with respect to the patient. In this regard, a conventional tracking system can track the spatial position of the imaging device and verify whether the imaging device is disposed at the desired spatial position to perform the imaging procedure.

A further embodiment of the present invention is to evaluate whether a device or instrument is placed correctly at a predefined position. Thus, the at least one image obtained is to verify whether the instrument or device is in fact located at a desired position, or whether its position (location and/or orientation) deviates from the desired position. The method according to the present invention may therefore comprise the following procedure:

A previous imaging acquisition procedure provides a three-dimensional image dataset, for example CT-dataset or an MR-dataset, of an anatomical structure of the patient. A desired trajectory for a medical instrument is defined by a practitioner with respect to the three-dimensional representation of the anatomical structure, along which the instrument is planned to be placed with respect to the anatomical structure.

In order to determine its spatial position, the instrument or a corresponding motorized support structure is provided with an optical marker array that can be detected in space by the optical tracking system. In case an initial positioning of the instrument along the desired trajectory is inaccurate, the tracking system deliver inaccurate results about the spatial position of the instrument. The tracking system may therefore locate the instrument as aligned along the desired trajectory, even though it is actually aligned with another trajectory. Without the inventive approach being applied, tracking system would locate the instrument at a position that deviates from its actual position by a shift.

In order to compensate for this possible inaccuracy, a specific example of the inventive approach is performed as follows:

Based on the information obtained so far, including the tracking information determined via the tracking system, the motorized support structure is controlled to move the instrument to align along the desired trajectory.

After the tracking system indicates that the instrument is aligned along the desired trajectory, the imaging device is controlled to acquire an image of the anatomical structure along with the instrument. In order to obtain an image that is meaningful in regards to a possible but yet unknown deviation, the imaging device is controlled to align in an imaging direction that is, as far as possible, perpendicular to the desired trajectory. The spatial positions of the imaging device is recognized by the tracking system via tracking markers attached to the imaging device.

The generated image, which may be a 2D-projection image, including the two-dimensional representations of the anatomical structure and the instrument then needs to be transformed into the three-dimensional coordinate system of the tracking system in order to evaluate possible deviations of the instrument's actual trajectory from the desired trajectory. As the spatial position of the imaging device with respect to the anatomical structure and the instrument is known, the spatial orientation of the image plane in the three-dimensional coordinate system can be determined. Further, the spatial position of the image plane along the imaging direction can also be determined on the basis of the instrument's spatial position. At this point, possible deviations between the actual trajectory and the desired trajectory should be rather small as compared to the overall distance between an emitter and a detector of the imaging device, such that possible positional errors are negligible here.

With the image and its content being transformed into the three-dimensional coordinate system, the possible deviation can then be calculated within the three-dimensional coordinate system.

Based on this information, the motorized support structure can be controlled to compensate for the detected deviation for the rest of the tracking procedure by a translational shift of the instrument until it aligns with the desired trajectory. The further tracking procedure can then be based on the corrected tracking information.

In a second aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method according to the first aspect. The invention may alternatively or additionally relate to a (physical, for example electrical, for example technically generated) signal wave, for example a digital signal wave, such as an electromagnetic carrier wave carrying information which represents the program, for example the aforementioned program, which for example comprises code means which are adapted to perform any or all of the steps of the method according to the first aspect. A computer program stored on a disc is a data file, and when the file is read out and transmitted it becomes a data stream for example in the form of a (physical, for example electrical, for example technically generated) signal. The signal can be implemented as the signal wave, for example as the electromagnetic carrier wave which is described herein. For example, the signal, for example the signal wave is constituted to be transmitted via a computer network, for example LAN, WLAN, WAN, mobile network, for example the internet. For example, the signal, for example the signal wave, is constituted to be transmitted by optic or acoustic data transmission.

The invention according to the second aspect therefore may alternatively or additionally relate to a data stream representative of the aforementioned program.

In a third aspect, the invention is directed to a computer-readable program storage medium on which the program according to the second aspect is stored. The program storage medium is for example non-transitory.

In a fourth aspect, the invention is directed to at least one computer (for example, a computer), comprising at least one processor (for example, a processor) and at least one memory (for example, a memory), wherein the program according to the second aspect is running on the processor or is loaded into the memory, or wherein the at least one computer comprises the computer-readable program storage medium according to the third aspect.

In a fifth aspect, the invention is directed to a medical system, comprising:

a) the at least one computer according to the fourth aspect;

b) at least one electronic data storage device storing at least the patient data; and c) an imaging device for acquiring image data of the patient, wherein the at least one computer is operably coupled to the at least one electronic data storage device for acquiring, from the at least one data storage device, at least the patient data, and the imaging device for issuing a control signal to the imaging device for controlling the operation of the imaging device on the basis of the patient data.

Alternatively or additionally, the invention according to the fifth aspect is directed to a for example non-transitory computer-readable program storage medium storing a program for causing the computer according to the fourth aspect to execute the data processing steps of the method according to the first aspect.

For example, the invention does not involve or in particular comprise or encompass an invasive step which would represent a substantial physical interference with the body requiring professional medical expertise to be carried out and entailing a substantial health risk even when carried out with the required professional care and expertise.

More particularly, the invention does not involve or in particular comprise or encompass any surgical or therapeutic activity. The invention is instead directed as applicable to imaging procedures only. For this reason alone, no surgical or therapeutic activity and in particular no surgical or therapeutic step is necessitated or implied by carrying out the invention.

The present invention also relates to the use of the device/system or any embodiment thereof for conducting an image procedure. The use comprises for example at least the following steps:

patient data is acquired, describing information relating to a patient and having impact on the setting of at least one imaging parameter of the imaging device;

imaging parameter data is determined based on the patient data, describing a patient-specific setting of the at least one imaging parameter of the imaging device.

DEFINITIONS

In this section, definitions for specific terminology used in this disclosure are offered which also form part of the present disclosure.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term computer includes a server resource. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, such as an electromagnetic carrier wave carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. A step of "determining" as described herein for example comprises or consists of issuing a command to perform the determination described herein. For example, the step comprises or consists of issuing a command to cause a computer, for example a remote computer, for example a remote server, for example in the cloud, to perform the determination. Alternatively or additionally, a step of "determination" as described herein for example comprises or consists of receiving the data resulting from the determination described herein, for example receiving the resulting data from the remote computer, for example from that remote computer which has been caused to perform the determination. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device).

Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

A marker device can for example be a reference star or a pointer or a single marker or a plurality of (individual) markers which are then preferably in a predetermined spatial relationship. A marker device comprises one, two, three or more markers, wherein two or more such markers are in a predetermined spatial relationship. This predetermined spatial relationship is for example known to a navigation system and is for example stored in a computer of the navigation system.

In another embodiment, a marker device comprises an optical pattern, for example on a two-dimensional surface. The optical pattern might comprise a plurality of geometric shapes like circles, rectangles and/or triangles. The optical pattern can be identified in an image captured by a camera, and the position of the marker device relative to the camera can be determined from the size of the pattern in the image, the orientation of the pattern in the image and the distortion of the pattern in the image. This allows determining the relative position in up to three rotational dimensions and up to three translational dimensions from a single two-dimensional image.

The position of a marker device can be ascertained, for example by a medical navigation system. If the marker device is attached to an object, such as a bone or a medical instrument, the position of the object can be determined from the position of the marker device and the relative position between the marker device and the object. Determining this relative position is also referred to as registering the marker device and the object. The marker device or the object can be tracked, which means that the position of the marker device or the object is ascertained twice or more over time.

A marker holder is understood to mean an attaching device for an individual marker which serves to attach the marker to an instrument, a part of the body and/or a holding element of a reference star, wherein it can be attached such that it is stationary and advantageously such that it can be detached. A marker holder can for example be rod-shaped and/or cylindrical. A fastening device (such as for instance a latching mechanism) for the marker device can be provided at the end of the marker holder facing the marker and assists in placing the marker device on the marker holder in a force fit and/or positive fit.

The present invention is also directed to a navigation system for computer-assisted surgery. This navigation system preferably comprises the aforementioned computer for processing the data provided in accordance with the computer implemented method as described in any one of the embodiments described herein. The navigation system preferably comprises a detection device for detecting the position of detection points which represent the main points and auxiliary points, in order to generate detection signals and to supply the generated detection signals to the computer, such that the computer can determine the absolute main point data and absolute auxiliary point data on the basis of the detection signals received. A detection point is for example a point on the surface of the anatomical structure which is detected, for example by a pointer. In this way, the absolute point data can be provided to the computer. The navigation system also preferably comprises a user interface for receiving the calculation results from the computer (for example, the position of the main plane, the position of the auxiliary plane and/or the position of the standard plane). The user interface provides the received data to the user as information. Examples of a user interface include a display device such as a monitor, or a loudspeaker. The user interface can use any kind of indication signal (for example a visual signal, an audio signal and/or a vibration signal). One example of a display device is an augmented reality device (also referred to as augmented reality glasses) which can be used as so-called "goggles" for navigating. A specific example of such augmented reality glasses is Google Glass (a trademark of Google, Inc.). An augmented reality device can be used both to input information into the computer of the navigation system by user interaction and to display information outputted by the computer.

The invention also relates to a navigation system for computer-assisted surgery, comprising:

a computer for processing the absolute point data and the relative point data;

a detection device for detecting the position of the main and auxiliary points in order to generate the absolute point data and to supply the absolute point data to the computer;

a data interface for receiving the relative point data and for supplying the relative point data to the computer; and a user interface for receiving data from the computer in order to provide information to the user, wherein the received data are generated by the computer on the basis of the results of the processing performed by the computer.

A navigation system, such as a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) for example comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

Preferably, atlas data is acquired from an anatomical atlas which describes (for example defines, more particularly represents and/or is) a general three-dimensional shape of the anatomical body part. The atlas data therefore represents an atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data. The atlas data comprises image information (for example, positional image information) which can be matched (for example by applying an elastic or rigid image fusion algorithm) for example to image information (for example, positional image information) contained in medical image data so as to for example compare the atlas data to the medical image data in order to determine the position of anatomical structures in the medical image data which correspond to anatomical structures defined by the atlas data.

The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

For example, the atlas data includes information of the anatomical body part. This information is for example at least one of patient-specific, non-patient-specific, indication-specific or non-indication-specific. The atlas data therefore describes for example at least one of a patient-specific, non-patient-specific, indication-specific or non-indication-specific atlas. For example, the atlas data includes movement information indicating a degree of freedom of movement of the anatomical body part with respect to a given reference (e.g. another anatomical body part). For example, the atlas is a multimodal atlas which defines atlas information for a plurality of (i.e. at least two) imaging modalities and contains a mapping between the atlas information in different imaging modalities (for example, a mapping between all of the modalities) so that the atlas can be used for transforming medical image information from its image depiction in a first imaging modality into its image depiction in a second imaging modality which is different from the first imaging modality or to compare (for example, match or register) images of different imaging modality with one another.

In the field of medicine and of the present invention, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (for example so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. For example, the medical imaging methods are performed by the analytical devices. Examples for medical imaging modalities applied by medical imaging methods are: X-ray radiography, magnetic resonance imaging, medical ultrasonography or ultrasound, endoscopy, elastography, tactile imaging, thermography, medical photography and nuclear medicine functional imaging techniques as positron emission tomography (PET) and Single-photon emission computed tomography (SPECT), as mentioned by Wikipedia.

The image data thus generated is also termed "medical imaging data". Analytical devices for example are used to generate the image data in apparatus-based imaging methods. The imaging methods are for example used for medical diagnostics, to analyze the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumor represents an example of a change in an anatomical structure. If the tumor grows, it may then be said to represent an expanded anatomical structure. This expanded anatomical structure may not be detectable; for example, only a part of the expanded anatomical structure may be detectable. Primary/high-grade brain tumors are for example usually visible on MRI scans when contrast agents are used to infiltrate the tumor. MRI scans represent an example of an imaging method. In the case of MRI scans of such brain tumors, the signal enhancement in the MRI images (due to the contrast agents infiltrating the tumor) is considered to represent the solid tumor mass. Thus, the tumor is detectable and for example discernible in the image generated by the imaging method. In addition to these tumors, referred to as "enhancing" tumors, it is thought that approximately 10% of brain tumors are not discernible on a scan and are for example not visible to a user looking at the images generated by the imaging method.

BRIEF DESCRIPTION OF THE DRAWINGS

In the following, the invention is described with reference to the appended figures which give background explanations and represent specific embodiments of the invention. The scope of the invention is however not limited to the specific features disclosed in the context of the figures, wherein.

DESCRIPTION OF EMBODIMENTS

Figure 1:
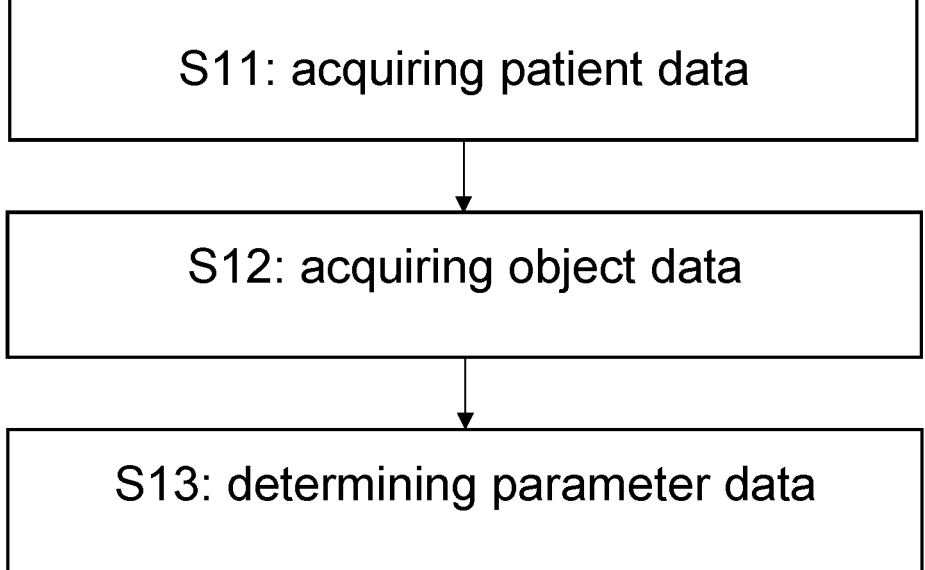
FIG. 1 illustrates the basic steps of the method according to the present invention

FIG. 1 shows the basic steps of a method in accordance with the present invention.

In a first step, patient data is acquired which describes the patient 5 and/or a later medical procedure performed on the patient 5, and which is stored in a database/data storage device 3 in communication with an imaging device 4.

In a further, second step, imaging parameter data is determined on the basis of the retrieved patient data, wherein the imaging parameter data defines a patient-specific setting of the at least one imaging parameter of the imaging device 4.

Figure 2:
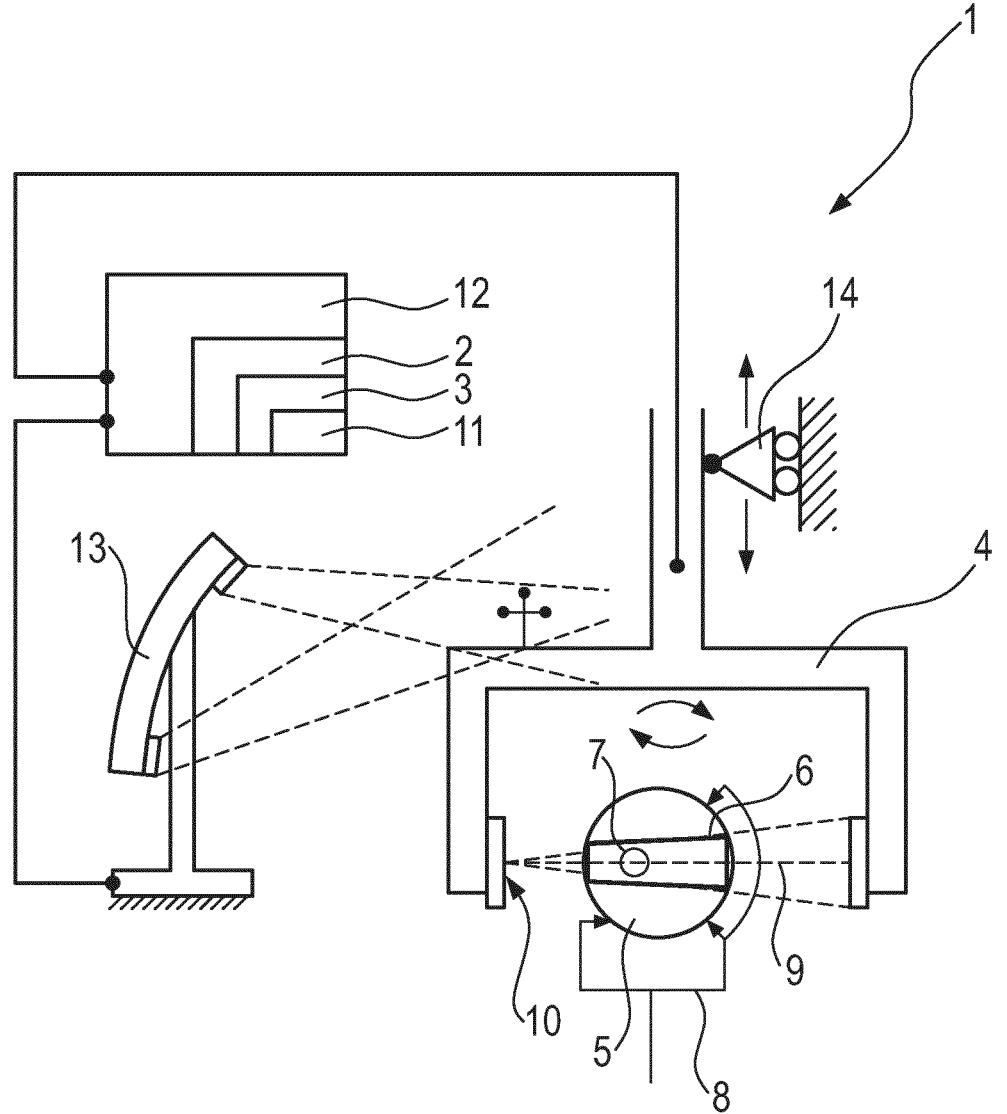
FIG. 2 shows a system that implements the method according to the present invention.

FIG. 2 shows an exemplary system 1 in which the above described method is implemented. System 1 comprises a CBCT scanner 4 including a radiation source (not indicated) with a collimator opening 10, which emits a radiation beam that extends along a trajectory 9 towards a radiation detector (not indicated) of the scanner 4. The opening of the collimator 10 is configured to shape the radiation beam, such that an image-dataset of the exam region 6 including an anatomical structure 7 of interest is obtained after the imaging procedure has been performed. In the shown example, a medical head-holder 8 is used to hold the head of the patient 5 at an invariant spatial position. Consequently, the collimator 10 has to shape the radiation beam such that the radiation beam does not intersect with the head-holder 8 as this may cause artifacts within the received image-dataset.

In the shown example, the CBCT-scanner 4 can be moved in two dimensions, i.e. has two degrees of freedom: with the help of a motorized carrier 14, the scanner 4 can be moved in a horizontal direction, wherein the scanner 4 can be also rotated around a horizontal axis, such that a volumetric (3D) image dataset of the region 6 is obtained after a full rotation of the scanner 4 around the patient 5. With the scanner 4 positioned with respect to the patient 5 as shown in FIG. 2, the radiation beam would sooner or later intersect with the head-holder 8 which may therefore cause artifacts in the later images. Thus, it is desirable to reposition the scanner 4 with respect to the patient 5 so that no interference between the radiation beam and the head-holder 8 occurs. This would require that the scanner 4 is repositioned with respect to the patient 5. As the spatial position of the target structure 7 as well as the spatial position and shape of the imaging region 6 with respect to the patient's anatomy has been defined and stored beforehand on a data storage device 3, an imaging parameter relating to the position of the scan trajectory 9 with respect to the patient 5 and with respect to the head-holder 8 is altered, so that the radiation beam does not intersect with the head-holder 8 during the imaging acquisition procedure. In this respect, it is important to know the spatial position of the scanner 4 with respect to the patient 5 and with respect to the head-holder 8. While the patient 5 and the head-holder 8 may be provided with a tracking reference for being spatially tracked, or may take a spatially invariant and known spatial position within a co-ordinate system of the medical tracking system 13, scanner 4 may feature a tracking reference (not indicated) which can be spatially detected via a camera array of the tracking system 13.

Based on the obtained patient data, the computer 2 of the navigation system 12 which is coupled to both, the tracking system 13 and the scanner 4 can control the motorized carrier 14 as well as further (not shown) parameter-setting devices.

Figure 3:
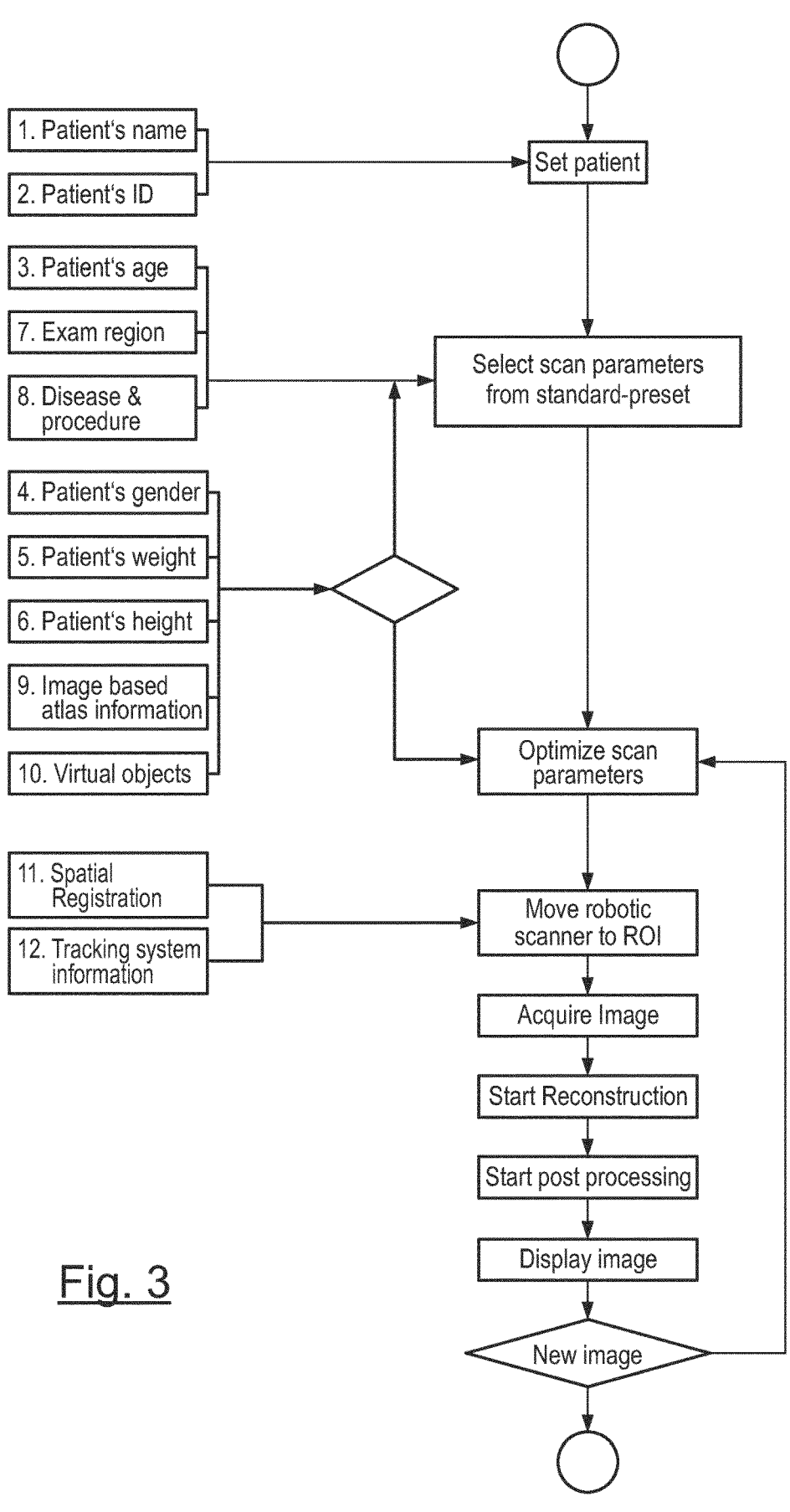
FIG. 3 shows an exemplary image acquisition workflow encompassing the method according to the present invention.

FIG. 3 shows how the present invention may be embedded within an image acquisition procedure. In a first step, a dataset of the patient 5, which is stored in a database 11 on the electronic data storage device 3, is selected by inputting the patient name or patient ID. Based on previously acquired information relating to the patient's age, the patient's exam region and/or the patient's type of disease and/or type of an associated treatment procedure, imaging parameters of the scanner 4 are set to an according default value. In a further step, information as to a patient's gender, the patient's height, the patient's weight, the position, size and/or shape of the anatomical structure 7 retrieved from an anatomical atlas, as well as a desired beam trajectory 9 stored as a virtual object registered to the patient (image-)dataset, the selected imaging parameters are optimized. With the patient 5 being spatially registered with respect to the scanner 4, and with the scanner 4 being tracked by the tracking system 13, the scanner 4 can be moved to the desired spatial position with respect to the patient 5 to acquire an image(-dataset) of the desired exam region 6. In case it is desirable to obtain another image with different imaging parameters, the optimization process can be repeated for obtaining a new image(-dataset).

The invention claimed is:

1. A computer-implemented method in a system including a computer having a processor and a non-transitory memory device operatively coupled with the processor for automatically determining by the processor executing program logic stored in the non-transitory memory device a setting of at least one imaging parameter of an imaging device, the method comprising:

receiving, at the processor of the computer of the system, patient data describing information relating to a patient and having impact on the setting of the at least one imaging parameter of the imaging device, the information relating to the patient comprising at least one of:
the patient's age;
the patient's gender;
the patient's weight;
the patient's height;
a type of disease of the patient and/or a type of an associated treatment procedure; and/or
a position, size and/or shape of a region to be imaged;
receiving, at the processor of the computer of the system, object data describing a spatial orientation of an object of interest associated with anatomy of the patient, the object of interest comprising at least one of:
a medical implant, device or instrument that will be depicted in at least one image to be acquired with the imaging device; and/or a trajectory for a medical implant, device, or instrument;
automatically determining, by the processor of the computer of the system, imaging parameter data based on the patient data and the object data, the imaging parameter data describing a patient-specific setting of the at least one imaging parameter of the imaging device taking into account the spatial orientation of the object of interest, the at least one imaging parameter of the imaging device comprising an orientation of a scan trajectory and/or of the imaging device, the orientation extending substantially perpendicularly with respect to a longitudinal direction defined for the object of interest, for the patient's anatomy and/or for objects coupled with the patient's anatomy; and
generating a control signal for controlling operation of the imaging device to image the patient to acquire an image of the patient using the patient-specific setting described by the automatically determined imaging parameter data.

2. The method according to claim 1, further comprising acquiring the patient data from an associated medical navigation system operably coupled to the imaging device.

3. The method according to claim 2, wherein the acquiring the patient data comprises selecting a dataset of the patient, wherein the dataset of the patient comprises at least one of a name of the patient and/or an identification of the patient.

4. The method according to claim 1, wherein the at least one imaging parameter of the imaging device is selected for a plurality of 2D- or 3D-images to be acquired via the imaging device, wherein the plurality of images comprises:
a series of images acquired at predefined intervals over a period of time or over a predefined route section of the imaging device moving relative to the patient, or
a group of images having substantially the same imaging direction or substantially perpendicular imaging directions.

5. The method according to claim 4, wherein determining imaging parameter data comprises adjusting, based on the object data and/or on a second subset of information relating to the patient, at least one predetermined imaging parameter setting included in the preset, wherein the second subset comprises at least one of:
gender information relating to the patient's gender;
weight information relating to the patient's weight;
height information relating to the patient's height; and/or
a spatial registration of the patient with respect to previously acquired image data.

6. The method according to claim 4, further comprising assigning different values of the same imaging parameter to different images.

7. The method according to claim 1, wherein determining imaging parameter data involves selecting, based on a first subset of information relating to the patient, a preset of at least one predetermined imaging parameter setting, the preset being selected from a plurality of predetermined presets which are in particular stored on a database.

8. The method according to claim 1, wherein imaging device is a x-ray-imaging-device which is spatially tracked by a medical tracking system operably coupled to the medical navigation system.

9. The method according to claim 1, further comprising:
acquiring current position data describing a current orientation of the imaging device with respect to the patient's anatomy;
determining target position data based on the current position data and the imaging parameter data, describing a target orientation of the imaging device with respect to the patient's anatomy for acquiring image data of the patient with the determined patient-specific setting of the at least one imaging parameter.

10. The method according to claim 9, further comprising controlling a motorized carrier of the imaging device based on the current position data and the target position data to move the imaging device to the target orientation.

11. The method according to claim 9, further comprising acquiring current position data based on the patient data and the object data.

12. The method according to claim 1, further comprising controlling a motorized support holding a medical device or instrument based on tracking data acquired from a tracking system, to place the medical device or instrument in an orientation or on a trajectory defined with respect to the anatomy of the patient, wherein at least one image is acquired once the tracking system indicates that the medical device or instrument has reached the predefined orientation or trajectory, wherein a deviation of an actual orientation or trajectory of the medical device or instrument from the predefined orientation or trajectory is calculated on the basis of the at least one acquired image and the object data describing the predefined orientation or trajectory.

13. The method according to claim 1, further comprising defining a virtual object with respect to a spatial position or a trajectory for a medical implant, device, or instrument, or at least one landmark or region of interest of the anatomy of the patient.

14. A program logic stored in a non-transitory memory device of a computer device that when running on the computer device or when loaded onto the computer device, causes the computer device to perform a method comprising:

receiving patient data at a processor of the computer device, the patient data describing information relating to a patient and having impact on a setting of at least one imaging parameter of an imaging device, the information relating to the patient comprising at least one of:

the patient's age;
the patient's gender;
the patient's weight;
the patient's height;
a type of disease of the patient and/or a type of an associated treatment procedure; and/or
a position, size and/or shape of a region to be imaged;

receiving object data at the processor of the computer device, the object data describing a spatial orientation of an object of interest associated with anatomy of the patient, the object of interest comprising at least one of:

a medical implant, device or instrument that will be depicted in at least one image to be acquired with the imaging device; and/or
a trajectory for a medical implant, device, or instrument;

automatically determining by the processor of the computer device imaging parameter data based on the patient data and the object data, the imaging parameter data describing a patient-specific setting of the at least one imaging parameter of the imaging device taking into account the spatial orientation of the object of interest, the at least one imaging parameter of the imaging device comprising an orientation of a scan trajectory and/or of the imaging device, the orientation extending substantially perpendicularly with respect to a longitudinal direction defined for the object of interest, for the patient's anatomy and/or for objects coupled with the patient's anatomy; and generating a control signal for controlling operation of the imaging device to image the patient to acquire an image of the patient using the patient-specific setting described by the automatically determined imaging parameter data.

15. A medical system, comprising:

an imaging device configured to acquire image data of a patient;

at least one computer device comprising a non-volatile memory device and a processor configured to execute logic stored in the non-volatile memory device of the computer to perform a method comprising:

receiving, at the processor of the computer of the system, patient data describing information relating to a patient and having impact on a setting of at least one imaging parameter of the imaging device, the information relating to the patient comprising at least one of:

the patient's age;
the patient's gender;
the patient's weight;
the patient's height;
a type of disease of the patient and/or a type of an associated treatment procedure; and/or
a position, size and/or shape of a region to be imaged;

receiving, at the processor of the computer of the system, object data describing a spatial orientation of an object of interest associated with anatomy of the patient, the object of interest comprising at least one of:

a medical implant, device or instrument that will be depicted in at least one image to be acquired with the imaging device; and/or
a trajectory for a medical implant, device, or instrument;

automatically determining, by the processor of the computer of the system, imaging parameter data based on the patient data and the object data, describing a patient-specific setting of the at least one imaging parameter of the imaging device taking into account the spatial orientation of the object of interest, the at least one imaging parameter of the imaging device comprising an orientation of a scan trajectory and/or of the imaging device, the orientation extending substantially perpendicularly with respect to a longitudinal direction defined for the object of interest, for the patient's anatomy and/or for objects coupled with the patient's anatomy; and at least one electronic data storage device storing at least the patient data and the object data, wherein the at least one computer is operably coupled to:

the at least one electronic data storage device for acquiring, from the at least one data storage device, at least the patient data and the object data; and the imaging device for issuing a control signal to the imaging device for controlling operation of the imaging device to acquire an image of the patient using the patient-specific setting described by the automatically determined imaging parameter data.

* * * * *